United States Patent
Gaudout et al.

(10) Patent No.: US 12,403,171 B2
(45) Date of Patent: *Sep. 2, 2025

(54) PLANT EXTRACT HIGHLY CONCENTRATED IN SAFRANAL, PRODUCTION METHOD AND USES THEREOF

(71) Applicant: ACTIV'INSIDE, Beychac et Caillau (FR)

(72) Inventors: David Gaudout, Carignan de Bordeaux (FR); Stephane Rey, Montelimar (FR); Benoit Lemaire, Libourne (FR); Benjamin Moras, Montelimar (FR); Marion Dumoulin, Bordeaux (FR)

(73) Assignee: ACTIV'INSIDE, Beychac et Caillau (FR)

(*) Notice: Subject to any disclaimer, the term of this patent is extended or adjusted under 35 U.S.C. 154(b) by 423 days.

This patent is subject to a terminal disclaimer.

(21) Appl. No.: 18/100,700

(22) Filed: Jan. 24, 2023

(65) Prior Publication Data

US 2023/0165927 A1 Jun. 1, 2023

Related U.S. Application Data

(63) Continuation of application No. 16/320,847, filed as application No. PCT/EP2017/069200 on Jul. 28, 2017, now Pat. No. 11,590,193.

(51) Int. Cl.
| | | |
|---|---|---|
| *A61Q 19/00* | (2006.01) | |
| *A61K 8/9789* | (2017.01) | |
| *A61K 8/9794* | (2017.01) | |
| *A61K 31/11* | (2006.01) | |
| *A61K 36/88* | (2006.01) | |
| *A61P 15/10* | (2006.01) | |
| *A61P 25/22* | (2006.01) | |
| *A61P 25/24* | (2006.01) | |

(52) U.S. Cl.
CPC .......... *A61K 36/88* (2013.01); *A61K 8/9789* (2017.08); *A61K 8/9794* (2017.08); *A61K 31/11* (2013.01); *A61P 15/10* (2018.01); *A61P 25/22* (2018.01); *A61P 25/24* (2018.01); *A61Q 19/00* (2013.01); *A61K 2236/15* (2013.01); *A61K 2236/33* (2013.01); *A61K 2236/331* (2013.01); *A61K 2236/333* (2013.01); *A61K 2236/35* (2013.01)

(58) Field of Classification Search
CPC ............ A61K 2236/15; A61K 2236/33; A61K 2236/331; A61K 2236/333; A61K 2236/35; A61K 31/11; A61K 36/88; A61K 8/9789; A61K 8/9794; A61K 2236/37; A61K 2800/805; A61K 31/352; A61K 31/7032; A61K 36/185; A61K 36/28; A61K 36/752; A61K 8/9783; A61P 15/10; A61P 25/22; A61P 25/24; A61Q 19/00; A23L 29/035; A23L 33/105; A23V 2002/00; A23V 2200/322
See application file for complete search history.

(56) References Cited

U.S. PATENT DOCUMENTS

2023/0201297 A1* 6/2023 Gaudout .................. A61P 3/00
424/725
2025/0108084 A1* 4/2025 Gaudout ................. A61P 25/28

FOREIGN PATENT DOCUMENTS

| CN | 1293924 A | 5/2001 |
|---|---|---|
| FR | 2900053 A1 | 10/2007 |
| FR | 2961379 A1 | 12/2011 |
| FR | 2995185 A1 | 3/2014 |

* cited by examiner

*Primary Examiner* — Jeffrey T. Palenik
(74) *Attorney, Agent, or Firm* — Greer, Burns & Crain, Ltd.

(57) ABSTRACT

The invention concerns a plant extract obtained from saffron, with a safranal concentration, measured using the HPLC method, of a minimum of 0.2% in weight relative to the total dry matter weight. The invention also concerns a procedure for obtaining such an extract, as well as compositions including this extract, and its use.

12 Claims, 4 Drawing Sheets

PLANT EXTRACT HIGHLY CONCENTRATED IN SAFRANAL, PRODUCTION METHOD AND USES THEREOF

CROSS-REFERENCE TO RELATED APPLICATIONS

This application is a continuation application of U.S. patent application Ser. No. 16/320,847 filed Jan. 25, 2019 which is a 371 U.S. national stage application of PCT/EP2017/069200 filed Jul. 28, 2017 which claims a priority from French Patent Application FR 1657297 filed Jul. 28, 2016, the entire disclosure of these applications is herein incorporated by reference.

TECHNICAL FIELD

This invention relates to a new extract obtained from a plant-based raw material containing safranal, in particular saffron, the said extract having a higher safranal concentration than plant extracts currently known.

The invention also concerns a specific procedure which enables such an extract to be obtained, as well as compositions including this extract, and its uses.

Safranal can be extracted from several plants, such as *Crocus sativus, Centaurea sibthorpii, Centaurea consanguinea, Centaurea amanicola, Erodium cicutarium*, Chinese green tea, *Calycopteris floribunda, Crocus heuffelianus, Sambucus nigra, Gardenia jasminoides, Citrus limon, Cuminum cyminum* L., and *Achillea distans* but is mostly extracted from *Crocus sativus*, which is also known as saffron.

BACKGROUND

Saffron is a traditional spice which is typically cultivated in Iran. It has several uses, such as the treatment of mood disorders, premenstrual syndrome, erectile dysfunction, or for skincare, as is notably presented in Javadi B & al. "*A survey on saffron in major islamic traditional medicine books*" Iranian journal of basic medical sciences 2013; 16(1): 1-11. Several clinical studies seeking to demonstrate the effectiveness of saffron have been conducted over past years, particularly in regard to its use for treating depression and anxiety, as is the case in: Akhondzadeh S & al. "*Comparison of Crocus sativus L. and imipramine in the treatment of mild to moderate depression: a pilot double-blind randomized trial*" [*ISRCTN45683816*]. BMC Complement Altern Med 2004; 4: 12, or, more recently, in: Hausenblas H A & al. "*Saffron (Crocus sativus L.) and major depressive disorder: a meta-analysis of randomized clinical trials*". Journal of integrative medicine 2013; 11(6): 377-83.

Saffron (*Crocus sativus*) is composed of several molecules, including safranal, a volatile molecule which creates the spice's fragrance and which is recognized for its effectiveness in the aforementioned applications. The extracts used in prior art are mostly standardized at 2% safranal using UV spectrometry, in accordance with the standard ISO 3632-2:2010 (*Spices—Saffron (Crocus sativus L.)—Part 2: Test methods. ISO International standard;* 2010: 1-42). This standard describes a comprehensive analysis protocol, which consists of dissolving the saffron extract in water, stirring it, filtering it, and then taking a spectrophotometric reading at 330 nm. Nevertheless, this method can be criticized as the absence of the use of any solvents and/or specific reagents results in the quantification of molecules other than safranal, and so the reading does not reflect the actual safranal concentration of the extract.

Effectively, the analysis by HPLC (High Performance Liquid Chromatography) of the safranal in extracts, which was used in prior art, reveals actual concentrations between 30 and 1000 times lower than those obtained by analysis using UV spectrometry, in accordance with standard ISO 3632-2, and with significant variability in the correlation of the two methods, as demonstrated by the results presented in Table 1 below:

TABLE 1 comparison of the results obtained with two safranal measurement methods applied to several saffron extracts from prior art (results given as percentages in weight relative to the total weight of the dry matter of the extract).

| Saffron extract | Safranal ISO 3632-2: 2010 method | Safranal HPLC method |
|---|---|---|
| Saffron dry extract - Natac | 2.71 | 0.0650 |
| Saffron ES stigma - Plantex | 2.12 | 0.0040 |
| Saffr'Activ ® - Green Plant Extract | 2.32 | 0.0380 |
| Affron ® - Pharmactive | 2.90 | 0.0190 |

In reality, the plant extracts containing safranal, particularly the saffron extracts, which can be obtained using the procedures of prior art, have very small doses of safranal.

The measurement method is therefore important, as it leads to results which differ from those obtained using the prior measurement method via spectrometry which was systematically used to measure the safranal concentration of a product. This prior method, referenced as ISO3632-2: 2010, overestimates the safranal concentration, as demonstrated in this application, as well as in the 2017 publication by Garcia-Rodriguez et al., "*Comparative evaluation of an ISO 3632 method and an HPLC-DAD method for safranal quantity determination in saffron*". In this publication, the study was carried out using 390 saffron samples. The overestimation may be between 20 and 50 times. Hence, an extract with an indicated concentration of X % safranal using the reference measurement method ISO3632-2:2010, contains, in reality, much less safranal.

SUMMARY

The objective of this invention is to address this issue by proposing a saffron extract with a higher dose of safranal than current extracts.

In particular, the invention concerns a plant extract obtained from saffron, with a concentration measured, using the HPLC method, of a minimum of 0.2% safranal in weight relative to the total weight of the dry matter of the extract.

This extract can notably be obtained via a procedure including a thermal treatment step, particularly a specific procedure which includes the implementation of the following steps:
Possible drying of the raw material,
Grinding of the dried raw material,
Aqueous or hydroalcoholic extraction, or extraction using an organic solvent,
Impregnation of the extract obtained onto a support,
Thermal treatment of the extract.

This economical procedure, which is simple to implement, enables a saffron extract to be obtained with a concentration, measured using the HPLC method, of a minimum of 0.2% safranal in weight relative to the total weight of the dry matter of the extract.

Advantageously, such an extract contains an actual safranal concentration which is greater than that of the extracts currently known and hence offers greater effectiveness, especially for use in combating depression, anxiety, mood disorders, erectile dysfunctions and premenstrual disorders. The invention therefore also concerns saffron extract for these uses, in addition to cosmetic, food, nutritional and medicinal compositions containing saffron extract.

Other characteristics and benefits will emerge from the detailed description of the invention which will follow, with respect to the appended figures.

DETAILED DESCRIPTION

Figure 1:
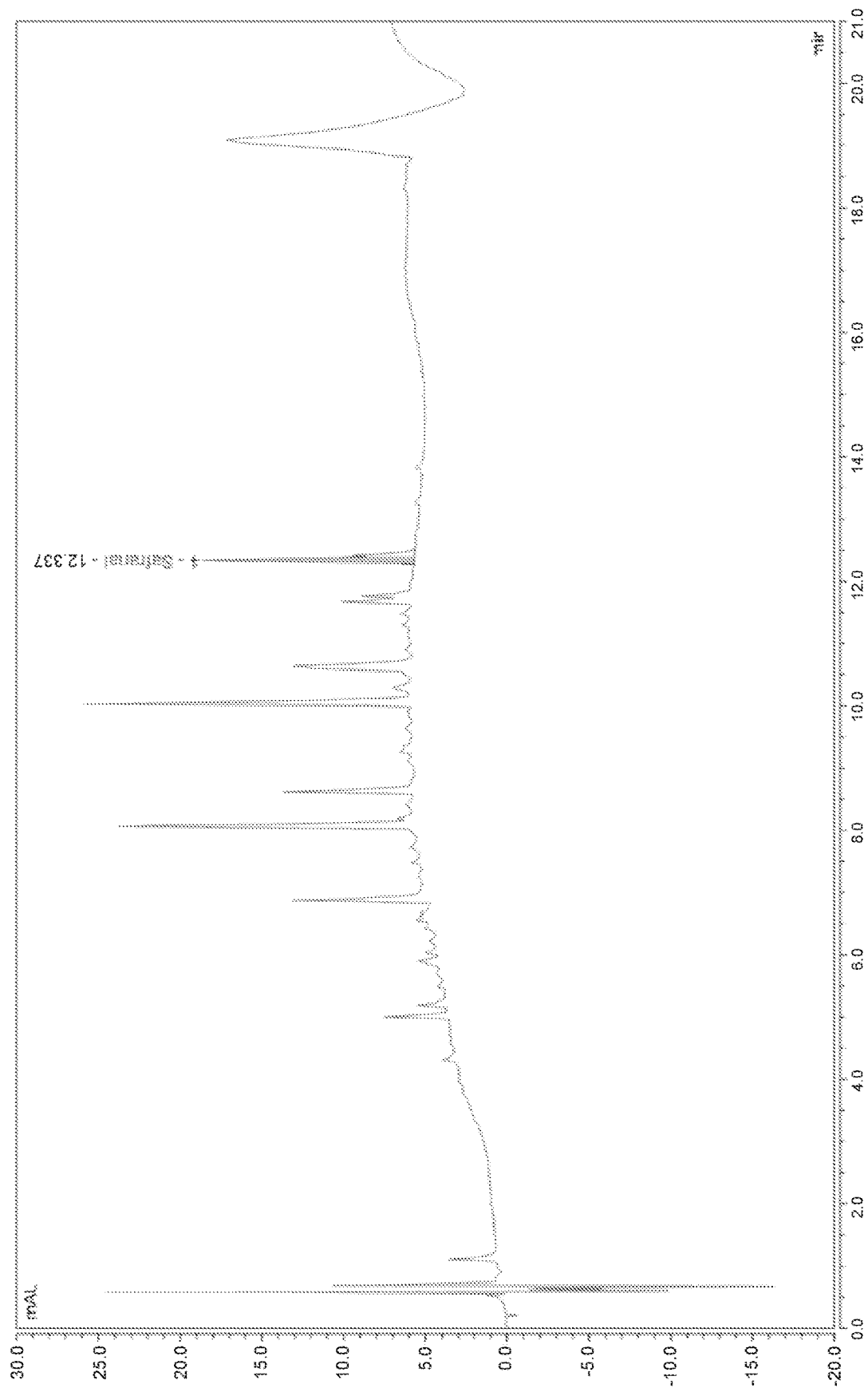
FIG. 1: chromatogram of the extract according to the invention from example 1, obtained via the UHPLC method.

Therefore, the invention concerns a plant extract obtained from a plant (or plant-based raw material) containing safranal, with a concentration, measured using the HPLC method, of a minimum of 0.2% safranal in weight relative to the total weight of the dry matter.

The expressions "plant extract obtained from a plant containing safranal" or "plant extract obtained from a plant-based raw material containing safranal" are understood to refer to at least one molecule or a set of several molecules from either an entire plant or part of a plant containing safranal. This may be from a specific selection of native molecules present in the plant or molecules obtained by any type of transformation of the said native molecules. The raw material used to obtain the extract can consist of either all or part of a plant containing safranal. If the plant containing the safranal is saffron, the plant extract according to the invention can in particular be obtained from saffron stigmas and/or petals and/or bulbs.

The extract according to the invention is not the raw material in itself. It is not considered to be a plant, part of a plant, a dried plant, a dried part of a plant, a plant sample or a dried plant sample. It is not an essential oil either.

The terms "plant containing safranal" or "raw material containing safranal" (the terms plant and plant-based raw material can be used equivalently within the meaning of the invention) are understood to refer to any plant containing safranal, in particular, *Crocus sativus, Centaurea sibthorpii, Centaurea consanguinea, Centaurea amanicola, Erodium cicutarium,* Chinese green tea, *Calycopteris floribunda, Crocus heuffelianus, Sambucus nigra, Gardenia jasminoides, Citrus limon, Cuminum cyminum* L., and *Achillea distans*. Preferentially, the plant containing safranal from which the extract according to the invention is obtained is *Crocus sativus* (saffron).

The extract according to the invention includes at least safranal, and the safranal is present at a concentration of at least 0.2% in terms of dry matter weight, measured using the HPLC method (High Performance Liquid Chromatography). The measurement method is of the utmost importance given that with another measurement method, namely with UV spectrometry (standard ISO 3632-2), the result obtained does not correspond to the actual safranal concentration given this method's lack of specificity.

The HPLC method for the analysis of molecules is a method known to skilled persons. It enables the precise identification and quantification of individual molecules.

Preferentially, the analysis method used for measuring the molecules contained in the extract according to the invention, in particular safranal, is a UHPLC method (Ultra High Performance Liquid Chromatography). This method also enables greater resolution and separation of compounds, as well as the detection of several compounds in the same chromatogram from a single sample.

According to a particularly suitable mode of implementation, the HPLC or UHPLC analysis method includes a prior preparation step for the sample, including the following steps:

Introduction of the saffron extract to be measured into a hydroalcoholic solution,
Magnetic stirring for at least 1 hour,
Ultrasonic bath for at least 5 minutes,
Filtration through a membrane, then injection.

The analysis method, after the preparation of the sample, traditionally then includes an elution step, then a detection step.

Elution is preferentially performed using a binary gradient. For example, the first solvent can be an organic solvent and an acid. Preferentially, formic acid in acetonitrile should be used.

For example, the second solvent can be an acidified aqueous solvent. Preferentially, formic acid in water should be used.

In addition to the safranal, the extract according to the invention can include other molecules, notably crocins and/or flavonoids, derived from kaempferol and/or derived from picrocrocin, particularly in the case of saffron extracts.

In the case whereby crocins are present, they should preferentially represent at least 1% of the dry matter weight of the extract, measured using the HPLC method.

In the case whereby flavonoids derived from kaempferol are present, they should preferentially represent at least 500 ppm of the dry matter weight of the extract, measured using the HPLC method.

In the case whereby picrocrocins are present, they should preferentially represent at least 0.5% of the dry matter weight of the extract, measured using the HPLC method.

Preferentially, the extract according to the invention is impregnated onto a support. The terms "support" or "bulking agent" within the meaning of the invention are understood to refer to any plant-, mineral-, or chemical-based food substance used as an ingredient or food additive which enables the impregnation and dilution of the extract of the invention.

The support may be selected from among the following components: maltodextrin, sugar, silica, and acacia gum, preference being given to maltodextrin.

When the extract is impregnated onto a support, the percentages of molecules present in the extract are expressed in terms of the dry matter weight of the extract, including the support. The extract according to the invention can be obtained by any means enabling at least 0.2% safranal to be obtained in terms of the dry matter weight of the extract. Preferentially, the extract according to the invention is obtained via a procedure including a thermal treatment step. This step can be implemented on the raw material at the beginning, during, or at the end of the procedure for obtaining the extract.

Thermal treatment, within the meaning of the invention, is understood to refer to heating up to a temperature to above ambient temperature. Preferentially, the thermal treatment step consists of a thermal treatment carried out for at least 2 hours, preferentially for at least 24 hours, at a temperature between 30° C. and 95° C., preferentially at a temperature between 30° C. and 60° C.

Thermal treatment may be carried out using any known means, notably in a chamber, in an oven, by cooking, pasteurizing or debacterialization. Preferentially, the thermal treatment is to be carried out in a chamber.

According to a particularly suitable mode of implementation, the plant extract according to the invention is obtained via a procedure including the implementation of the following steps, completed using saffron as a raw material:

Possible drying,
Grinding, preferentially between 50 and 500 μm,
Aqueous or hydroalcoholic extraction, or extraction using an organic solvent,
Impregnation of the extract obtained onto a support,
Thermal treatment.

The aqueous or hydroalcoholic extraction steps, or extraction using an organic solvent and impregnation of the extract obtained onto a support, constitute the known extraction procedure, named Tech'Care Extraction®.

The thermal treatment step can be carried out at any moment during this procedure, preferentially at the end of the procedure, on the raw material saffron, and completes the Tech'Care Extraction® procedure.

According to a particularly suitable mode of implementation, the thermal treatment step in the implementation of this procedure is a thermal treatment step in a chamber for at least 2 hours, even more preferentially for at least 24 hours at a temperature between 30° C. and 95° C., even more preferentially at a temperature between 30° C. and 60° C.

Grinding can be carried out by any suitable known means, particularly by a granulating mill, a pin mill or a hammer miller, with preference given to a pin mill.

The extraction step can be carried out by any suitable known means.

In the case of aqueous extraction, the ground substance is introduced into water at a ratio of 50 g/L.

In the case of hydroalcoholic extraction, the solvent can be ethanol, with preference given to ethanol at 60% v/v. The ground substance is introduced into the hydroalcoholic solution at a ratio of 50 g/L.

In the case of extraction using an organic solvent, the solvent can be methanol or ethyl acetate, with preference given to methanol at 30% v/v. The ground substance is introduced into the organic solvent at a ratio of 100 g/L.

After extraction, the procedure can also include an acidification step. This step consists of adding acid into the aqueous or hydroalcoholic solvent. It enables the pH of the extraction solution to be reduced to between 3 and 5. It can be carried out in the following conditions: adding citric acid or hydrochloric acid into the hydroalcoholic solvent to adjust the pH to 4.

The step of impregnation onto a support consists of adding a bulking agent into the extraction solution. The support or bulking agent can be selected from among the following components: maltodextrin, sugar, silica, and acacia gum, but maltodextrin is preferred.

After this impregnation step, the procedure can also include an emulsion step and/or an encapsulation step for the obtained extract. This step consists of high-speed stirring of the extraction solution containing the bulking agent and, possibly, the auxiliary substance. It can be carried out using auxiliary substances such as acacia gum, cyclodextrins, or fatty substances.

The extract according to the invention can be used alone or integrated into a cosmetic, food, nutritional or medicinal composition, at a ratio of 0.1 to 100% in terms of the dry matter weight of the composition. Preferentially, the extract according to the invention is present in the composition in a quantity which enables it to be administered to humans or animals at a minimum of 0.07 mg of extract according to the invention per kg of body weight per day, even more preferentially between 1.4 and 4.2 mg of extract according to the invention per kg of body weight per day.

The invention therefore concerns such a composition, preferentially a composition which is presented in the form of a capsule, tablet, soft capsule, stick, sachet, prepared dish, oil, lotion, cream or emulsion.

The compositions including an extract according to the invention may contain other suitable known components, such as excipients, which are selected depending on the form and intended use of the composition, or other active substances or active molecules.

The extract according to the invention and compositions including it may be used for several applications, particularly for preventing or treating depression and anxiety, or for preventing or treating mood disorders (pathological mood disorders), erectile dysfunctions, or premenstrual disorders.

The invention also concerns the extract for its use:
in the prevention or treatment of depression in humans or animals,
in the prevention or treatment of anxiety in humans or animals,
in the prevention or treatment of mood disorders in humans,
in the prevention or treatment of erectile dysfunction in humans (males),
in the prevention or treatment of premenstrual disorders in humans (females).

Advantageously, due to the high quantity of safranal it contains, which is greater than that of all existing extracts, the extract according to this invention offers great effectiveness for these applications. Furthermore, it is important to use an extract rather than a raw material in itself (an entire plant or part of a plant, dried or not), as the extracts according to the invention enable the bioavailability of active molecules to be increased as the latter are no longer locked in the plant matrix of the flower, and are more easily available to the organism. The presence of the support in the extract also allows for improved homogeneity of molecules which are of interest for the finished product.

The invention is currently illustrated with examples of extracts and procedures according to the invention (examples 1 and 2), comparative examples of extracts from prior art (examples 3A and 3B) and compositions.

For all examples, the measurement method for molecules in the extract, and particularly for safranal, is a UHPLC method, with the following characteristics:

1. Sample Preparation

Sample extraction using a hydroalcoholic solution. Magnetic stirring for at least 1 hour, then ultrasonic bath for at least 5 minutes. Filtration through a membrane, then injection.

2. HPLC Elution

Binary Gradient:
Solvent A (formic acid in MeCN)
Solvent B (formic acid in water)

3. Detection

| | |
|---|---|
| Crocins | 440 nm |
| Picrocrocin derivatives | 250 nm |
| Flavonoids | 350 nm |
| Safranal | 310 nm |

4. Standards

Trans-crocin-4-gentiobiose-gentobiose
Trans-crocin 3-gentiobiose-glucose
beta-cyclocitral
Kaempferol glucoside
Safranal Example 1: Extract According to the Invention A first extract example is an extract obtained via the implementation of the procedure, consisting of the implementation of the following steps:
use of *Crocus sativus* stigmas,
grinding using a pin mill, to 250 μm,
hydroalcoholic extraction using ethanol 60% v/v, at a ratio of 50 g of saffron per liter of hydroalcoholic solution,
impregnation on maltodextrin, introduced into the hydroalcoholic solution,
thermal treatment in a chamber for 48 hours at 40° C.

The obtained extract is measured for several molecules using the UHPLC method described in the foreword of the section pertaining to the examples.

The chromatogram obtained is presented in FIG. 1.
The extract is characterized by:
a safranal concentration of 0.238%,
a crocin concentration of 3.96%,
a picrocrocin derivative concentration of 1.08%, and
a flavonoid concentration of 0.25%.

Example 2: Extract According to the Invention

A second extract example is an extract obtained via the implementation of the procedure, consisting of the implementation of the following steps:
use of *Crocus Sativus* stigmas,
grinding using a pin mill, to 250 μm,
acidified aqueous extraction using hydrochloric acid at pH 4,
impregnation on acacia gum, introduced into the aqueous solution,
thermal treatment in a chamber for 72 hours at 40° C.

The obtained extract is measured for several molecules using the UHPLC method described in the foreword of the section pertaining to the examples.

Figure 2:
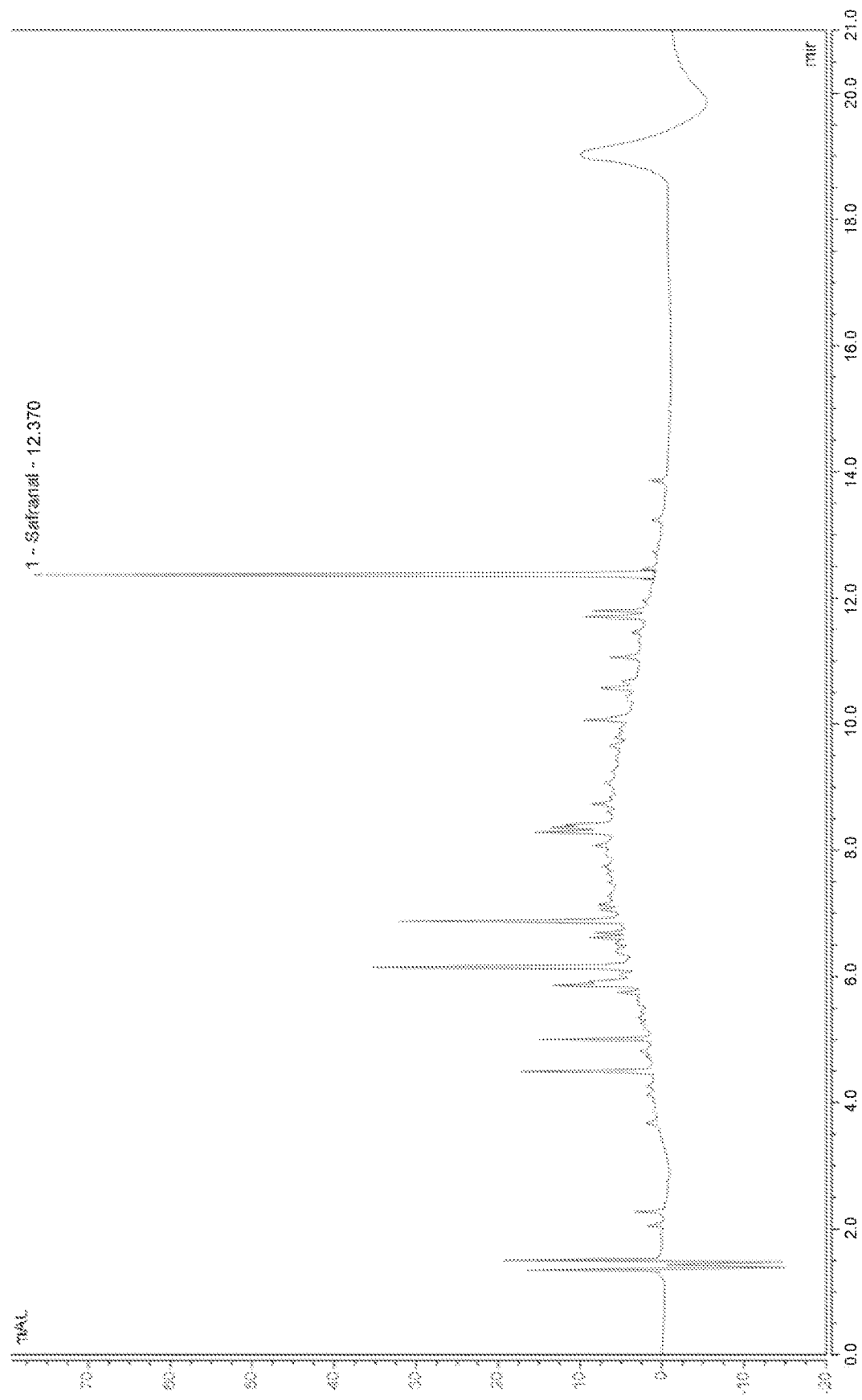
FIG. 2: chromatogram of the extract according to the invention from example 2, obtained via the UHPLC method.

The chromatogram obtained is presented in FIG. 2.
The extract is characterized by:
a safranal concentration of 0.73%,
a crocin concentration of 1.0%,
a picrocrocin derivative concentration of 2.93%, and
a flavonoid concentration of 0.57%.

Example 3: Extract According to the Invention

A third example of extract is an extract obtained via the implementation of the procedure, consisting of the implementation of the following steps:
use of *Crocus Sativus* stigmas,
grinding using a pin mill, to 250 μm,
first thermal treatment in a chamber for 2 to 6 hours at 105° C.
second thermal treatment in a chamber for 2 to 6 hours at 140° C.
hydroalcoholic extraction using ethanol 60% v/v, at a ratio of 50 g of saffron per liter of hydroalcoholic solution,
impregnation on maltodextrin, introduced into the hydroalcoholic solution,
freeze-drying of the liquid extract
The extract is characterized by:
a safranal concentration of 0.39%,
a crocin concentration of 2.31%,
a picrocrocin derivative concentration of 1.37%, and
a flavonoid concentration of 0.24%.

Example 3A: Extract Obtained by Atomization (Exclusive of the Invention)

Figure 3A:
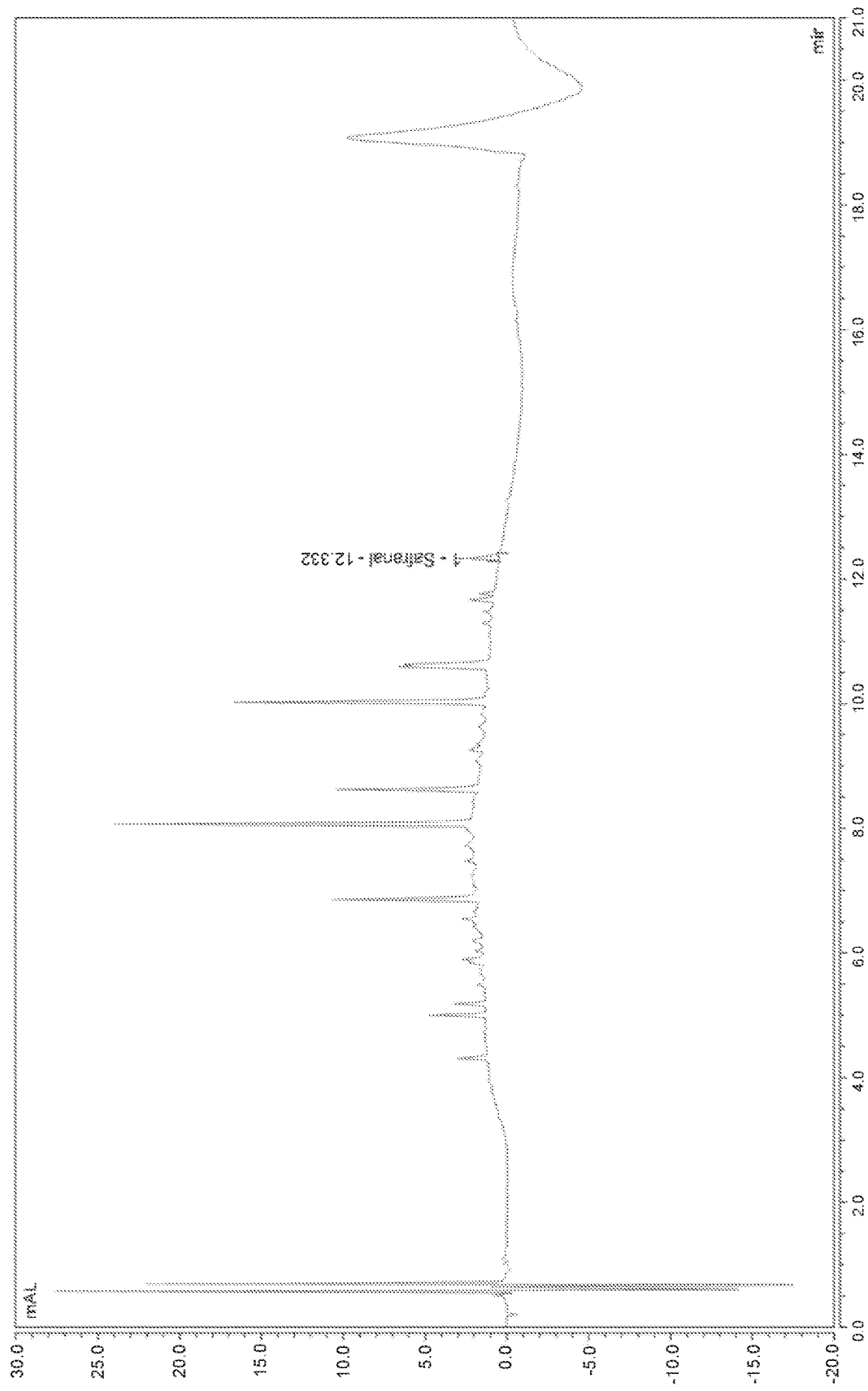
FIG. 3A: chromatogram of an extract from prior art according to example 3A (obtained without thermal treatment) obtained via the UHPLC method.

A first extract counterexample is an extract obtained via the implementation of the procedure, consisting of the implementation of the following steps:
use of *Crocus sativus* stigmas,
grinding using a pin mill, to 250 μm,
hydroalcoholic extraction using ethanol 60% v/v, at a ratio of 50 g of saffron per liter of hydroalcoholic solution,
impregnation on maltodextrin, introduced into the hydroalcoholic solution,
spray-drying of the liquid extract.
The chromatogram obtained is presented in FIG. 3A.
The obtained extract is characterized by:
a safranal concentration of 0.028%,
a crocin concentration of 4.98%,
a picrocrocin derivative concentration of 1.26%, and
a flavonoid concentration of 0.24%

Example 3B: Extract Obtained by Freeze-Drying (Exclusive of the Invention)

Figure 3B:
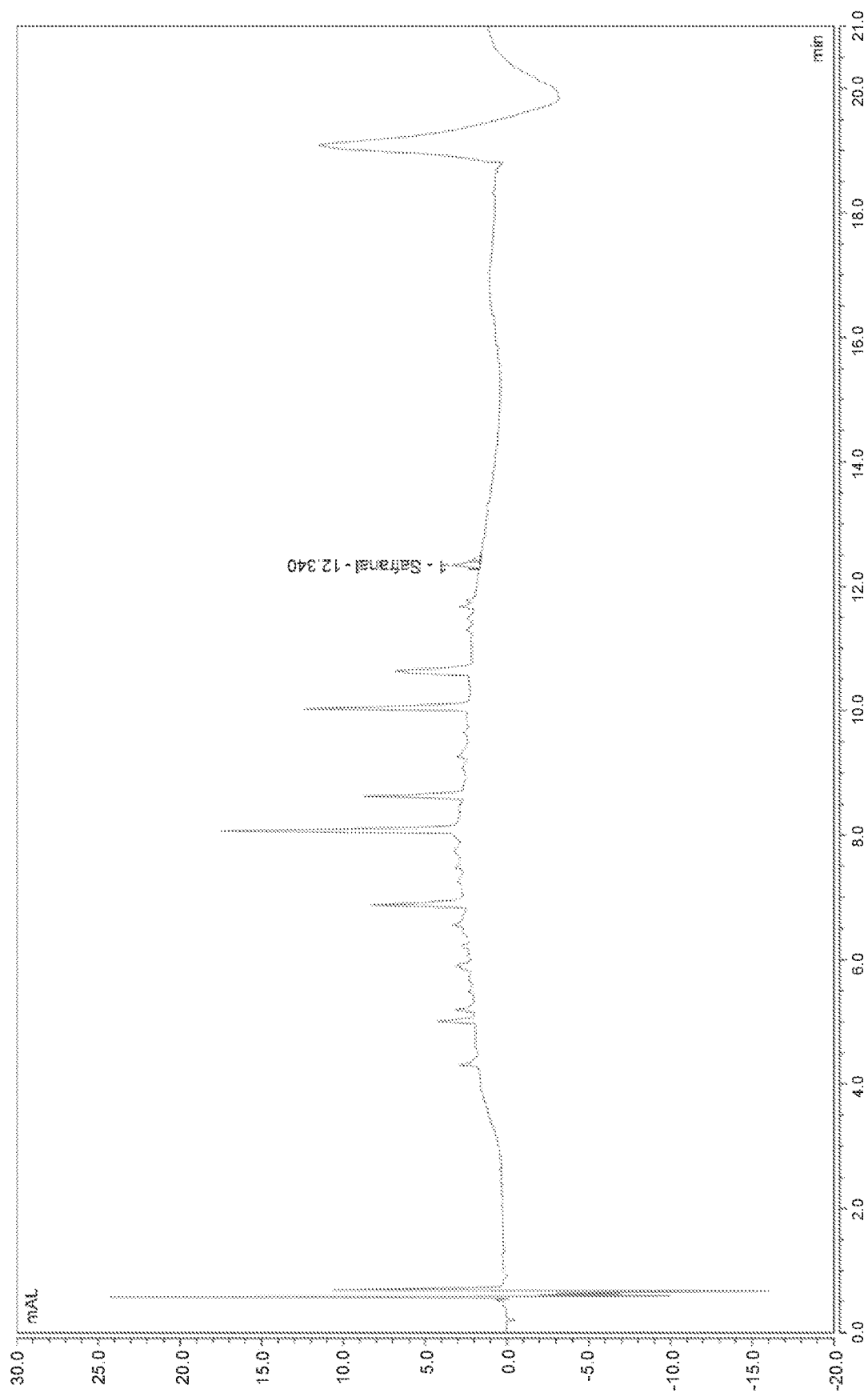
FIG. 3B: chromatogram of an extract from prior art according to example 3B (obtained without thermal treatment) obtained via the UHPLC method.

A second extract counterexample is an extract obtained via the implementation of the procedure, consisting of the implementation of the following steps:
use of *Crocus sativus* stigmas,
grinding using a pin mill, to 250 μm,
hydroalcoholic extraction using ethanol 60% v/v, at a ratio of 50 g of saffron per liter of hydroalcoholic solution,
impregnation on maltodextrin, introduced into the hydroalcoholic solution,
freeze-drying of the liquid extract.
The chromatogram obtained is presented in FIG. 3B.
The extract is characterized by:
a safranal concentration of 0.038%,
a crocin concentration of 4.40%,
a picrocrocin derivative concentration of 1.15%, and
a flavonoid concentration of 0.22%.

Example 4: Example of Nutritional Composition for Human Use

Example 4 is a 150 mg capsule composed of:
The extract according to the invention from example 1:15 mg
Maltodextrin: 135 mg The composition is obtained by mixing the components in the traditional conditions known to the skilled person, the mixture then being transferred into a capsule, also according to the traditional conditions.

The advised dosage is 2 capsules per day.

Example 5: Example of Medication for Human Use

Example 5 is a 1500 mg tablet composed of:
The extract according to the invention from example 2: 20 mg,
Sorbitol: 1430 mg,
Magnesium stearate: 27 mg,
Brilliant blue FCF lacquer E133: 20 mg,
Acesulfame K (E950): 1.5 mg,
Sodium saccharin (E954): 1.5 mg.

The composition is obtained by mixing the components in the traditional conditions known to the skilled person, the mixture then being compressed, also according to the traditional conditions.

The advised dosage is 1 tablet per day.

Example 6: Example of Nutritional Composition for Animal Use

Example 6 is a 300 mg tablet composed of:
The saffron extract from example 1: 6 mg,
Microcrystalline cellulose: 135 mg,
Magnesium stearate: 10 mg.

The composition is obtained by mixing the components in the traditional conditions known to the skilled person, the mixture then being compressed, also according to the traditional conditions.

The advised dosage is 1 tablet per day.

Example 7: Cosmetic Composition for Topical Application in the Form of a Day Cream This composition is presented in the form of a cream to be applied to skin.

It is composed of:
The extract according to the invention from example 1: 10 mg,
Preservative: 0.5%,
Perfumes: 0.6%,
Fatty phase+aqueous phase: 97.4%.

The fatty phase is composed of an emulsifier and triglycerides. The aqueous phase is composed of water combined with pyrrolidone carboxylic acid.

The composition is obtained by adding the saffron extract from example 1, while stirring, with the preservatives and perfumes to the aqueous phase, over a period of 10 minutes. The aqueous phase is then itself added while stirring to the fatty phase and is mixed for 30 minutes.

We claim:

1. A thermally treated, encapsulated plant extract in powder form containing at least 0.2% of safranal by weight as measured by HPLC, the thermally treated encapsulated plant extract obtained by the method comprising:
   a) extracting a plant-based raw material containing safranal, wherein the plant-based raw material is selected from the group consisting of *Crocus sativus, Centaurea sibthorpii, Centaurea consanguinea, Centaurea amanicola, Erodium cicutarium*, Chinese green tea, *Calycopteris floribunda, Crocus heuffelianus, Sambucus nigra, Gardenia jasminoides, Citrus limon, Cuminum cyminum* L., and *Achillea distans* with an extraction solution to provide a liquid extract;
   b) impregnating the liquid extract onto a bulking agent selected from the group consisting of maltodextrin, sugars, silica, and acacia gum to form an encapsulated plant extract; and
   c) subjecting the encapsulated plant extract to thermal treatment.

2. The thermally treated, encapsulated plant extract of claim 1, wherein the plant-based raw material is *Crocus sativus* stigmas, petals and/or bulbs.

3. The thermally treated, encapsulated plant extract of claim 1, wherein the thermal treatment step is carried out for at least 2 hours at a temperature between 30° C. and 95° C.

4. The thermally treated, encapsulated plant extract of claim 1, wherein the thermal treatment step is performed at a temperature between 30° C. and 60° C.

5. The thermally treated, encapsulated plant extract of claim 1, wherein the thermal treatment step is carried out for a period of at least 24 hours.

6. The thermally treated, encapsulated plant extract of claim 1, wherein the thermal treatment step is carried out in a chamber, oven, by cooking, pasteurization or debacterialization.

7. The thermally treated, encapsulated plant extract of claim 1, wherein the extraction solution is aqueous or hydroalcoholic.

8. The thermally treated, encapsulated extract of 1, wherein the thermally treated, encapsulated extract contains a derivative of kaempferol and/or picrocrocin.

9. A cosmetic, food, nutritional or medicinal composition comprising between 0.1 and 100% by weight of the thermally treated, encapsulated plant extract of claim 1.

10. The cosmetic, food, nutritional or medicinal composition of claim 9, wherein the composition is in the form of a capsule, tablet, soft capsule, stick, sachet, prepared dish, oil, lotion, cream or emulsion.

11. The cosmetic, food, nutritional or medicinal composition of claim 9, wherein the composition is useful for treating depression, anxiety, erectile dysfunction or premenstrual disorder.

12. A method for ameliorating one or more symptoms of depression, anxiety, erectile dysfunction or premenstrual disorder in a subject, the method comprising administering to the subject the cosmetic, food, nutritional or medicinal composition of claim 9.

* * * * *